US007858925B2

(12) United States Patent
Kinahan et al.

(10) Patent No.: US 7,858,925 B2
(45) Date of Patent: Dec. 28, 2010

(54) CALIBRATION METHOD AND SYSTEM FOR PET SCANNERS

(75) Inventors: Paul E. Kinahan, Seattle, WA (US); Keith C. Allberg, Weare, NH (US); Robert K. Doot, Seattle, WA (US); Catherine M. Lockhart, Greenbank, WA (US); Wendy McDougald, Mercer Island, WA (US)

(73) Assignee: University of Washington, Seattle, WA (US)

( * ) Notice: Subject to any disclaimer, the term of this patent is extended or adjusted under 35 U.S.C. 154(b) by 15 days.

(21) Appl. No.: 12/472,285

(22) Filed: May 26, 2009

(65) Prior Publication Data

US 2009/0283668 A1 Nov. 19, 2009

Related U.S. Application Data

(63) Continuation-in-part of application No. 11/485,872, filed on Jul. 13, 2006, now Pat. No. 7,615,740.

(60) Provisional application No. 60/791,161, filed on Apr. 11, 2006.

(51) Int. Cl.
 *G01D 18/00* (2006.01)
(52) U.S. Cl. .............................. 250/252.1; 250/363.03
(58) Field of Classification Search .............. 250/252.1, 250/363.01, 363.02, 363.03, 363.04
See application file for complete search history.

(56) References Cited

U.S. PATENT DOCUMENTS

| 4,333,010 A | 6/1982 | Miller |
| 4,401,108 A | 8/1983 | Galkin |
| 4,430,258 A | 2/1984 | McFarland |

(Continued)

FOREIGN PATENT DOCUMENTS

EP 1416297 A1 5/2004

OTHER PUBLICATIONS

"Atomlab™ 100 Plus Dose Calibrator," © 2008 Biodex Medical Systems, Inc., <http://www.biodex.com/radio/dosecal/dose_265feat.htm> [retrieved Apr. 16, 2009], 3 pages.

(Continued)

*Primary Examiner*—David P Porta
*Assistant Examiner*—Marcus H Taningco
(74) *Attorney, Agent, or Firm*—Christensen O'Connor Johnson Kindness PLLC

(57) ABSTRACT

A method, system and kit for calibrating a PET scanner is disclosed. A first aliquot (10) containing a quantity of a radionuclide dispersed in a solid matrix material is provided, wherein the first aliquot is sized and configured to be received for measurement by a conventional dose calibrator. A second aliquot (200) containing a quantity of the radionuclide dispersed in the solid matrix material is sized configured to be scanned in a PET scanner. The radionuclide/matrix materials in the first and second aliquots are obtained from the same batch of material, such that the two quantities have the same radioactivity density, or are obtained from different cross-calibrated batches of material. In a method, the first aliquot is placed in a does calibrator (36) and the radioactivity is measured. The second aliquot is scanned in the PET scanner (190) and the intensity of the image is correlated with the known radioactivity measured by the dose calibrator and used to calibrate the PET scanner.

21 Claims, 8 Drawing Sheets

U.S. PATENT DOCUMENTS

| | | | |
|---|---|---|---|
| 4,506,155 A | | 3/1985 | Suzuki |
| 5,241,181 A | * | 8/1993 | Mertens et al. ........ 250/363.03 |
| 6,251,059 B1 | | 6/2001 | Apple |
| 2002/0156338 A1 | | 10/2002 | Menuhr |
| 2003/0216609 A1 | * | 11/2003 | Dell et al. ..................... 600/34 |
| 2004/0119030 A1 | * | 6/2004 | Kalas et al. .............. 250/493.1 |
| 2004/0260143 A1 | | 12/2004 | Reilly |
| 2005/0029465 A1 | | 2/2005 | Lemer |
| 2005/0047114 A1 | | 3/2005 | Harrell |
| 2005/0107698 A1 | | 5/2005 | Powers |
| 2008/0272284 A1 | | 11/2008 | Rietzel |
| 2009/0072152 A1 | | 3/2009 | Chen |

OTHER PUBLICATIONS

Frouin, V., et al., "Correction of Partial-Volume Effect for PET Striatal Imaging: Fast Implementation and Study of Robustness," The Journal of Nuclear Medicine 43(12):1715-1726, Dec. 2002.

Kim, C.K., et al., "Standardized Uptake Values of FDG: Body Surface Area Correction is Preferable to Body Weight Correction," The Journal of Nuclear Medicine 35(1):164-167, Jan. 1994.

Soret, M., et al., "Partial-Volume Effect in PET Tumor Imaging," The Journal of Nuclear Medicine 48(6):932-945, Jun. 2007.

"Vial/Syringe Dipper," © 2008 Biodex Medical Systems, Inc., <http://www.biodex.com/radio/dosecal/dose_242.htm> [retrieved Apr. 16, 2009], 1 page.

"Y90 Calibration Source," © 2009 QSA Global, <http://www.aurigamedical.com/auto/calibration.asp> [retrieved Apr. 16, 2009], 1 page.

Zasadny, K.R., and R.L. Wahl, "Standardized Uptake Values of Normal Tissues at PET With 2-[Fluorine-18]-Fluoro-2-deoxy-D-glucose: Variations With Body Weight and a Method for Correction," Radiology 189(3):847-850, Dec. 1993.

* cited by examiner

CALIBRATION METHOD AND SYSTEM FOR PET SCANNERS

CROSS-REFERENCES TO RELATED APPLICATIONS

This application is a continuation-in-part of U.S. patent application Ser. No. 11/485,872, filed Jul. 13, 2006, which claims the benefit of Provisional Application No. 60/791,161, filed Apr. 11, 2006, the disclosures of which are hereby expressly incorporated by reference in their entirety.

STATEMENT OF GOVERNMENT LICENSE RIGHTS

This invention was made with Government support under SAIC-Frederick, Inc prime Contract No. HHSN261200800001E and SAIC-Frederick, Inc. Subcontract No. 24XS036 Task Order 004, through the National Cancer Institute. The Government has certain rights in the invention.

BACKGROUND

Medical imaging technology has made remarkable advances in recent years, including developments and improvements in computed tomography ("CT"), magnetic resonance imaging ("MRI"), functional magnetic resonance imaging ("fMRI"), single photon emission computed tomography ("SPECT"), and positron emission tomography ("PET").

PET imaging has revolutionized imaging of internal biological regions by providing functional images of a patient or other region of interest. Positron emission tomography is a nuclear medicine medical imaging technique that produces a three-dimensional image or map of functional processes in the body, e.g., imaging that illuminates chemical and metabolic activity in the patient. The role of PET imaging in oncology research and patient care, in particular, is growing due to the ability of PET to add unique functional information to that obtained by conventional anatomical imaging modalities, for example CT.

PET scanning is an emissive technique wherein a short-lived radioactive tracer isotope, chemically combined with a metabolically active molecule such as a sugar, is injected into the subject. The metabolically active molecule becomes concentrated in the tissues of interest, concentrating the tracer isotope in regions of such activity. After injecting the isotope, the patient is placed on the scanner. As the injected isotope decays it emits a positron that annihilates with an electron, producing a pair of gamma rays or photons that travel in opposite directions. In general terms, the emitted photons are detected when they reach a scintillator material in the scanning device, creating a burst of light that is detected by photomultiplier tubes.

The detection technique relies on the coincident detection of the pair of photons to identify valid signals. Photons that are not detected within a few nanoseconds of each other are ignored. A straight line through the locations in the detector where the coincident photons are detected is called the line of response ("LOR"). The location of the positron emission is therefore known to lie somewhere along the LOR. The PET scanner uses the pair detection events and the LORs to map the density of the tracer isotope within the body. In a typical system, the images are generated along parallel slices separated by about 5 mm and the images are then combined to produce a three-dimensional image or model of the region of interest. The resulting map shows where the tracer isotope has become concentrated, identifying regions of metabolic activity in the body.

A dose calibrator (radioisotope calibrator) is a device used in nuclear medicine that measures the total energy of a specific radionuclide in units of Curies (Ci), millicuries (mCi), or microcuries (μCi). It includes a hollow, lead-shielded cylinder, into which radionuclides are lowered for measurement. Such devices can be programmed for specific radioisotopes, or adjusted for isotopes not preprogrammed. A dose calibrator is commonly used to obtain measurements of the total radioactivity of isotopes prior to administration to patients undergoing nuclear medicine diagnostic imaging procedures or radioisotope therapy procedures. Regulatory authorities specify when a radioisotope dose calibrator will be used and the timing of required quality control checks (constancy, accuracy, linearity, and geometrical dependence).

Currently, a dose calibration source standard is used for calibration of the dose calibrator. The calibration source includes a cylindrical vial comprising a predetermined amount of the radionuclide to be calibrated, together with a decay calendar, which allows a user to determine the amount of radionuclide present in the source at the time of testing. The current dose calibration source standards are designed to closely approximate the geometry of unit dose radiopharmaceuticals dispensed in vials by radiopharmacies and may therefore only partially meet the standards implied in CEI-IEC 61145 "Calibration and Usage of Ionization Chamber Systems for Assay of Radionuclides;" CEI-IEC 1303 "Medical Electrical Equipment—Radionuclide Calibrators—Particular Method of Describing Performance;" ANSI N42.13-1986 "Calibration and Usage of 'Dose Calibrator' Ionization Chambers for the Assay of Radionuclides;" and 10 CFR 35.50 "Possession, Use, Calibration, and Check of Dose Calibrators."

Nuclear medicine practitioners generally administer radiopharmaceuticals using a syringe. The practitioner places the syringe containing the radiopharmaceutical into the pre-calibrated dose calibrator to assay its content. The syringe has a different body shape from that of the calibration vials used as calibration standards and, due to the shape of the syringe and configuration of the dose calibrator, is positioned in the dose calibrator with the syringe body in a different location from the vial.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Aspects of the exemplary embodiment relate to a dose calibrator source standard which is designed to closely approximate the geometry of unit dose radiopharmaceuticals dispensed in syringe form which meets the above-mentioned CEI-IEC, ANSI, and CFR standards.

Current dose calibrator source standards are designed to approximate the geometry of a typical radiopharmaceutical multidose vial or radionuclide generator elution vial (10 milliliters volume and 30 milliliters volume, respectively). While a cylindrical vial was adequate a number of years ago, the dispensing of radiopharmaceuticals in a syringe for unit dosing no longer provides dose calibrator source standards that approximate radioactivity volume or physical geometry of a typical syringe assay. The exemplary dose calibrator source standard is designed to provide a National Institute of Science and Technology traceable standard where the radioactivity volume and physical geometry of the body of a syringe is reproduced, which may also serve as a vial standard.

Figure 1:
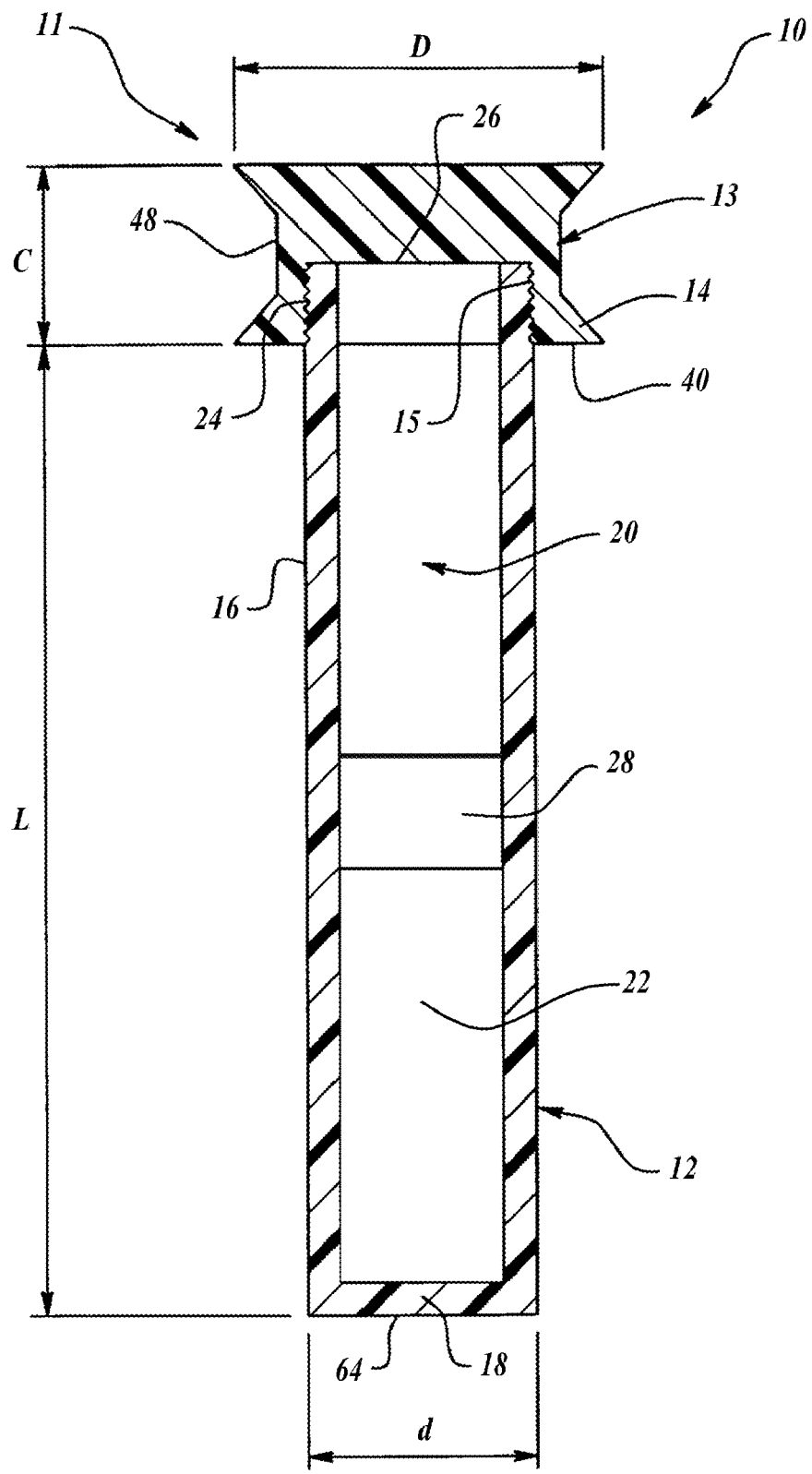
FIG. 1 is a side sectional view of a dose calibrator source standard according to a first aspect of the exemplary embodiment.

With reference to FIG. 1, a first embodiment dose calibrator source standard 10 according to the exemplary embodiment is illustrated. The source standard 10 includes a container 11 which includes a cylindrical encapsulation barrel 12 configured to mimic the barrel of a syringe and a closure member 13 mounted to the encapsulation barrel, which mimics the plunger of the syringe. The illustrated closure member 13 defines an enlarged diameter support member 14 in the form of a laterally extending annular flange and an interior socket 15. The encapsulation barrel 12 includes a cylindrical wall 16 of substantially uniform cross section which is closed at a lower end by a base 18. The base 18 may be integrally formed with the wall 16, for example by molding. The upper end of the barrel 12 is closed by the closure member 13 to define a sealed interior 20. A radioactive source-containing material 22 is sealed within the encapsulation barrel 12. The barrel 12 includes an exterior threaded portion 24 at an upper open end 26 which is configured for threadably engaging corresponding interior threads on the socket 15 of the closure member. A sealant material (not shown), may be applied to the threads to provide an airtight and tamper-resistant seal between the barrel 12 and the closure member 13. A void created between the radioactive source containing material 22 and the closure member 13 may be backfilled with an appropriate polymer matrix 28, such as epoxy, urethane, silicone, or other appropriate material. While FIG. 1 shows the interior having an air space above the matrix 28, it is contemplated that the entire interior space 20 above the radioactive material 22 may be backfilled with matrix 28, leaving no air space.

Figure 2:
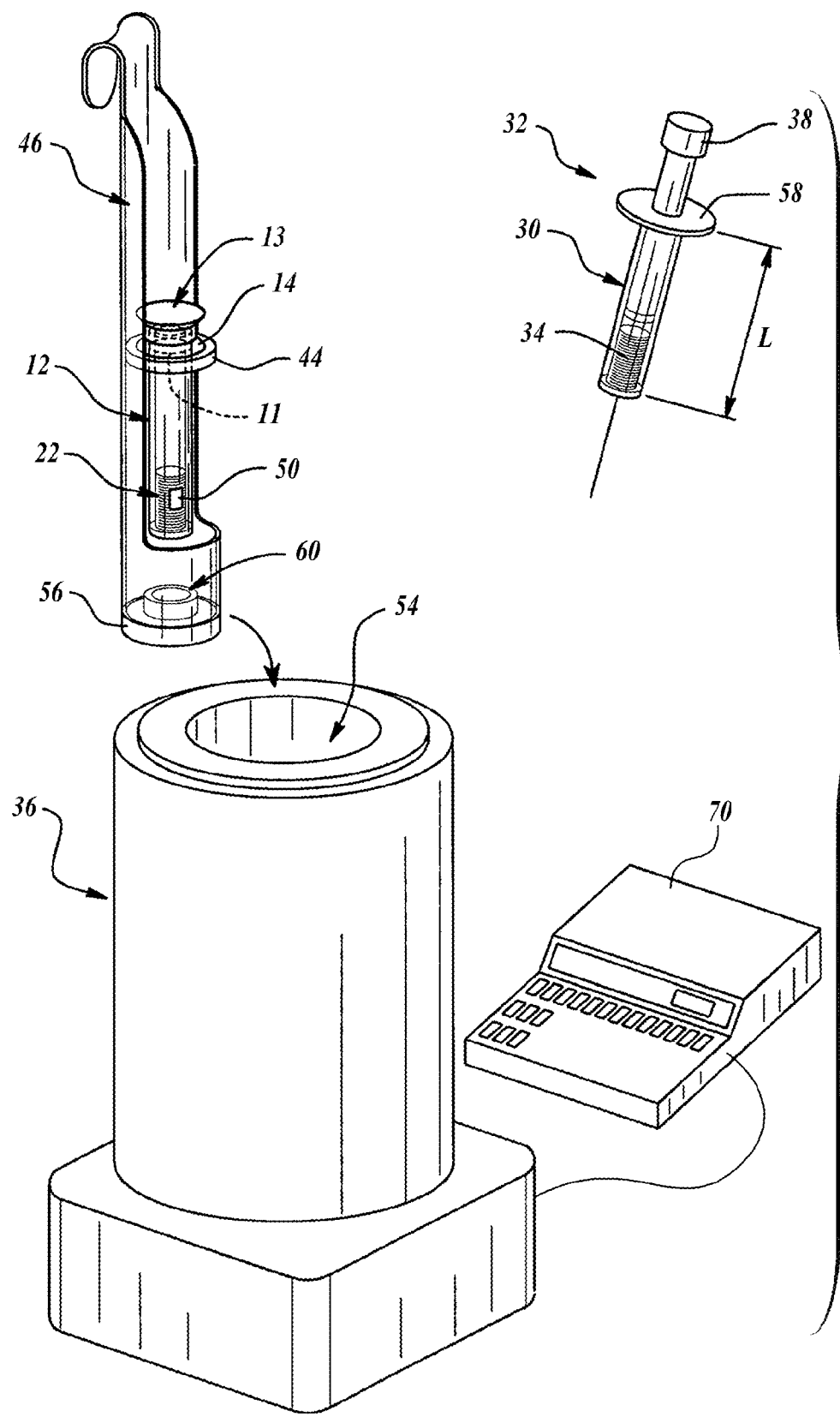
FIG. 2 is a perspective view of the dose calibrator source standard being lowered into a dose calibrator with a scoop and a syringe containing a radionuclide to be calibrated.
Figure 3:
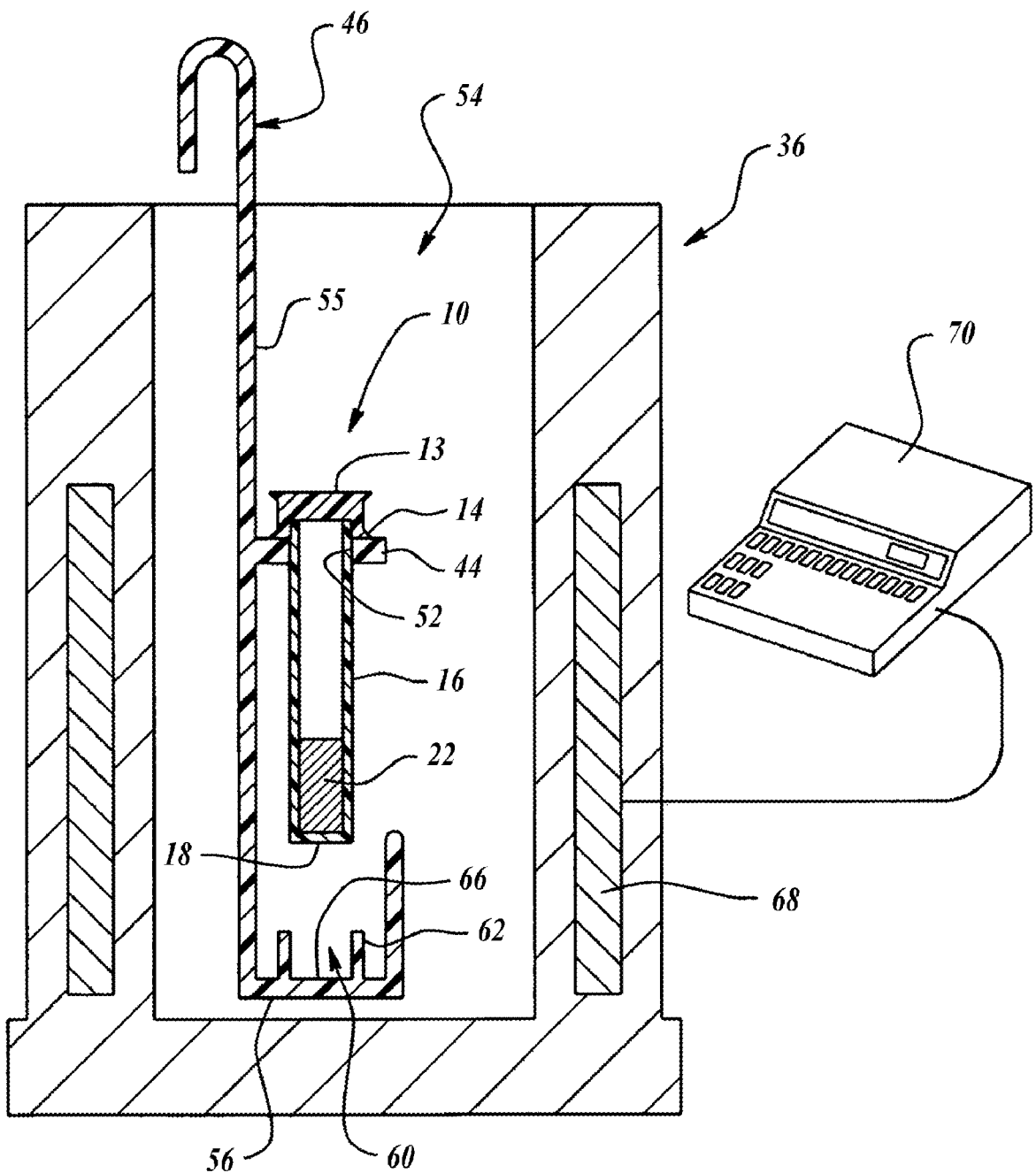
FIG. 3 is a side sectional view of the dose calibrator source standard, dose calibrator, and scoop of FIG. 2, during a calibration.

The encapsulation barrel 12 and closure member 13 may be formed from a plastic polymer, such as Lucite™, or a low Z material, such as aluminum or other material which is transmissive to substantially all radiation emitted from the source. The barrel 12 has an outer diameter d and length L (as measured from the base to support member) similar to that of a barrel 30 of a syringe 32 containing a radiopharmaceutical 34 which is to be tested in a dose calibrator 36 of the type shown in FIGS. 2 and 3. In general the sidewall 16 has a length L which is at least twice a diameter d of the base 18. For example, the diameter d and length L may be within +/−10% of the actual syringe dimensions, e.g., within +5%, or identical thereto. The radioactive nuclide-containing material 22 thus occupies dimensions and a volume comparable to that of the radiopharmaceutical liquid 34 to be tested.

In one embodiment, the outer barrel diameter d may be up to about 2.5 cm (1 inch) and the barrel length L up to about 10 cm (4 inches). The volume of the interior 20 may be from about 3 to about 10 cm$^3$. The closure member 13 may have a height C and/or other dimensions which are similar to that of a plunger 38 of the syringe 32 for ease of handling although in general, the dimensions of the closure member are not critical. In operation, the illustrated support member 14 extends radially outwardly from the barrel wall 16 to define an annular surface 40 suitable for seating on a syringe shelf 44 of an ion chamber syringe scoop 46 of the type shown in FIGS. 2 and 3. While in one embodiment, surface 40 is annular, it is also contemplated that the surface may be of any suitable configuration for resting on the shelf 44. For example, the surface 40 may be defined by two (or more) radially extending wings. The surface 40 may extend about 0.3 cm to about 2 cm from the barrel 12, e.g., at least about 0.5 cm. The exact dimension may depend on the configuration of the scoop 46. The illustrated support member 14 includes an annular generally concave cavity 48, spaced from the support surface, for ease of transporting the dose standard 10.

While in the illustrated embodiment, the support member 14 is defined by the closure member 13, in alternate embodiments, the support member may be defined by the barrel 12, e.g., by being integrally formed therewith, for example as a lip.

The radioactive source-containing material 22 may include one or more radionuclides encapsulated in a suitable solid matrix material. Exemplary nuclides include gamma radiation emitters, such as sodium 22 (Na-22), cobalt 57 (Co-57), cobalt 60 (Co-60), germanium 68 (Ge-68), barium 133 (Ba-133), thallium 204 (TI-204), and cesium 137 (Cs-137) in appropriate quantities for serving as a standard for calibration. The matrix material may comprise an epoxy, silicone, urethane, ceramic, or similar type of matrix material in which the radionuclide may be uniformly dispersed.

To form the source standard 10, appropriate quantities of a radionuclide and a liquid polymer composition are mixed to disperse the radionuclide uniformly. The polymer composition may include a polymer resin together with accelerators, crosslinking agents, and the like which cause the polymer to harden when cured (e.g., by UV-curing or an ambient cure). The liquid radionuclide/polymer composition is placed in the barrel 16 and cured to form a solid 22. The barrel 16 may then be backfilled with polymer matrix material, which is also cured. The barrel is then sealed to the closure member 13, for example, by placing a small amount of the polymer matrix material around the threads 24 and threadably connecting the closure member 13 to the barrel 12. The assembled source standard 10 is then calibrated e.g., against a traceable National Institute of Standards (NIST) solution. A custom decay calendar may then be derived and affixed by means of a label 50 to the source standard 10 or to a shielding container in which the source standard 10 is shipped and stored.

The source standard can be used in two different calibration modes. To calibrate the dose calibrator 36 for use with syringes (first mode), the source standard 10 is supported on the syringe shelf 44 of a suitably configured syringe scoop 46. The scoop shelf 44 engages the support member surface 40. In particular, the scoop shelf 44 has a generally centrally positioned circular aperture 52 therein which is sized to accommodate the barrel 12 therethrough but which is smaller than the maximum diameter D of the support surface 40. The scoop 46 is then lowered into an ion chamber 54 of the dose calibrator 36 by a vertically extending handle 55. The shelf 44 of the scoop is vertically spaced along the handle from a base 56 of the scoop by a sufficient distance such that the syringe 30 can subsequently be accommodated by the scoop while being supported with a lip 58 of the syringe barrel resting on the shelf 44. The illustrated scoop base 56 includes an upwardly open vial cup 60 comprising a cylindrical wall 62 of suitable diameter to receive a conventional cylindrical vial source standard (not shown) therein. The exemplary base 18 of the source standard 10 is sized to fit within the vial cup 54 and has a planar lower surface 64 whereby the source standard 10 can rest on a correspondingly sized planar base surface 66 of the vial cup 60 with the source standard 10 in an upright position (second mode). In this way, the source standard 10 can be used for calibrating the dose calibrator 34 for syringes (when suspended on the shelf 44), or for vials (when seated in the cup 60), simulating, for example, a 10 cc multidosing vial. In both cases, the radiation source-containing material 22 is correctly positioned so as to be in a comparable location in the ion chamber 54 of the dose calibrator 34 to the actual dose of radiopharmaceutical 34 in the vial or syringe 32. The radiation emitted by the source standard 10 is detected by a radiation detector 68 and a measure of the radiation, such as the amount of radiation emitted per unit time, is recorded on suitable instrumentation 70.

The exemplary source standard 10 thus described meets or exceeds the American National Standards Institute (ANSI) safety classification of 97C22312 as described in Publication ANSI/HPS N43.6-1997 "Sealed Radioactive Source—Classification."

The source standard 10 may be color-coded for easy identification, e.g., as follows: TABLE-US-00001 Green: Cs-137 Red: Co-57 Blue: Co-60 Yellow: Na-22 Black: Ba-133 White: Ge-68 Orange Tl-204

Figure 4:
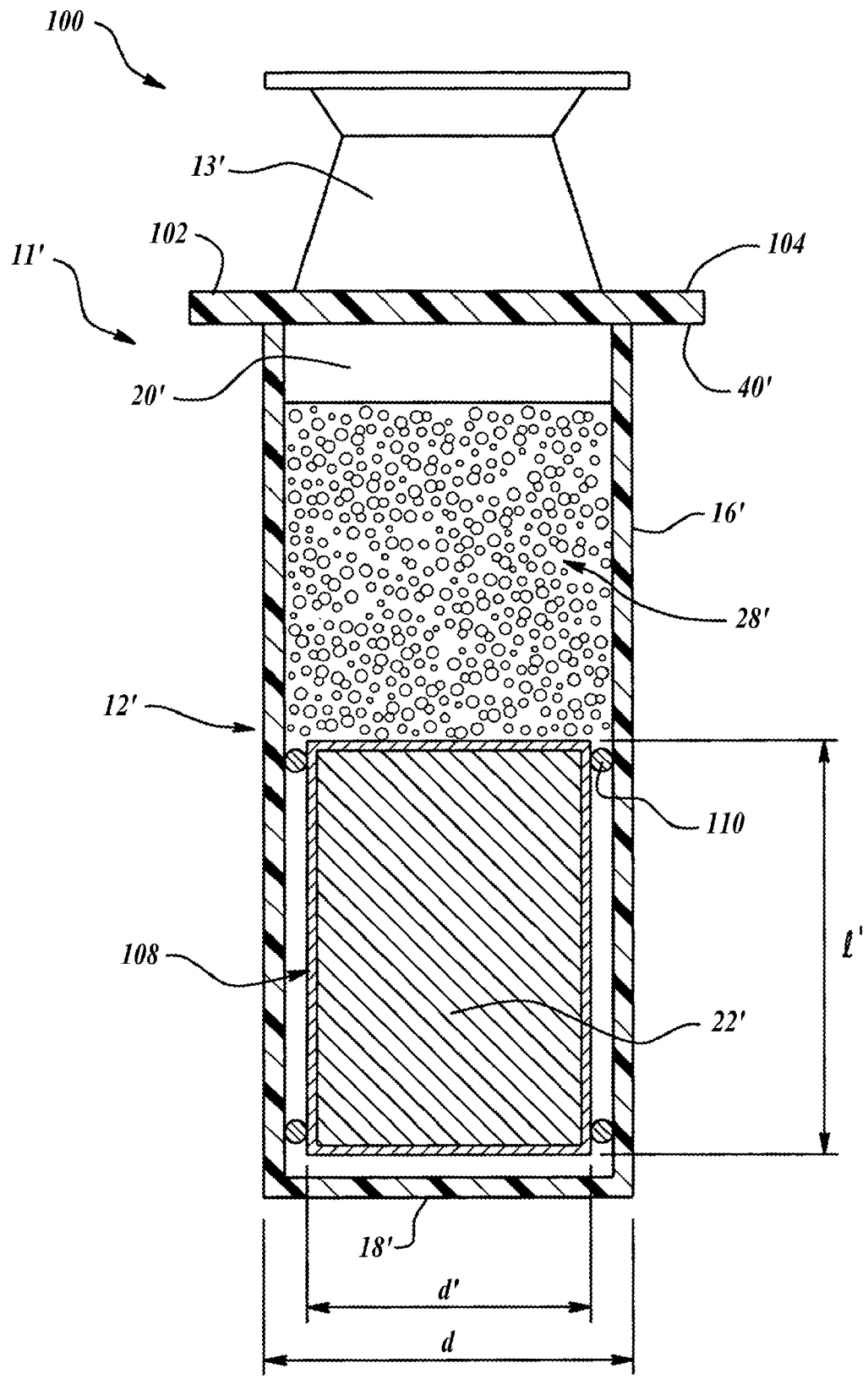
FIG. 4 is a side sectional view of a dose calibrator source standard according to a second aspect of the exemplary embodiment.

FIG. 4 illustrates another embodiment of a source standard 100 which may be similarly configured to source standard 10, except as noted. In this embodiment, similar elements are identified by a primed suffix (') and new elements are accorded new numbers. In this embodiment, a support surface 40' is defined by two finger wings 102, 104, which extend approximately 1-2 cm beyond the barrel diameter d. The wings may be integrally formed with the barrel 12' or with a cover member 13' in the form of a mock plunger, which seals the open end of the barrel 12'. The finger wings 102, 104 extend in opposite directions to support the source standard 10 in existing ion chamber scoops, such as scoop 46.

The embodiment of FIG. 4 provides a double encapsulation for the source material 22. An outer encapsulation is provided by the barrel and mock plunger 13', while inner encapsulation is provided by a cylindrical housing 108 made of a plastic polymer or low Z material, such as aluminum. The housing 108 is sized to fit within the interior 20' of the barrel. For example, the housing 108 is no greater than about 2 cm (0.8 inches) in diameter d' and no greater than about 4 cm (about 1.50 inches) in length l' and may be centered in the barrel with the use of o-rings 110 secured around the housing prior to insertion into the outer barrel 12'. The radiation source-containing material is sealed within the housing 108. This embodiment provides for double encapsulation of the matrix 22 with metal, plastic, or a combination of both. However, it is also contemplated that the outer container 11' need not be sealed and that the radiation source-containing material may be sealed within the container 11' by virtue of the inner housing 108.

The void created between the radioactive source encapsulation and the mock plunger may be backfilled with an appropriate matrix 28 such as epoxy, urethane, silicone, or other appropriate material.

In this embodiment, the outer container 11' may be formed from a hollowed out rod of material which is machined exteriorly to define the mock plunger. The container 11' is sealed at the end to form a base 18' after insertion of the inner housing 108 containing radioactive material.

Calibration of PET Scanner

Positron emission tomography ("PET") is an emissive imaging technique that is used heavily in clinical oncology (medical imaging of tumors and the search for metastases) and is also used in human brain and heart research. In PET a short-lived radioactive tracer isotope is chemically combined with a metabolically active molecule and injected into the patient or test subject, for imaging. The metabolically active molecule is preferentially taken up by metabolically active tissue, concentrating the tracer isotope in such regions. As the radioisotope decays it emits a positron that will typically travel a very short distance before it annihilates with an electron, producing a pair of photons having an energy of 511 kEv (gamma rays), that travel in opposite directions. In simplified terms, the emitted photons are detected when they strike a scintillator material in the scanning device, creating a burst of light that is detected by photomultiplier tubes.

Figure 5:
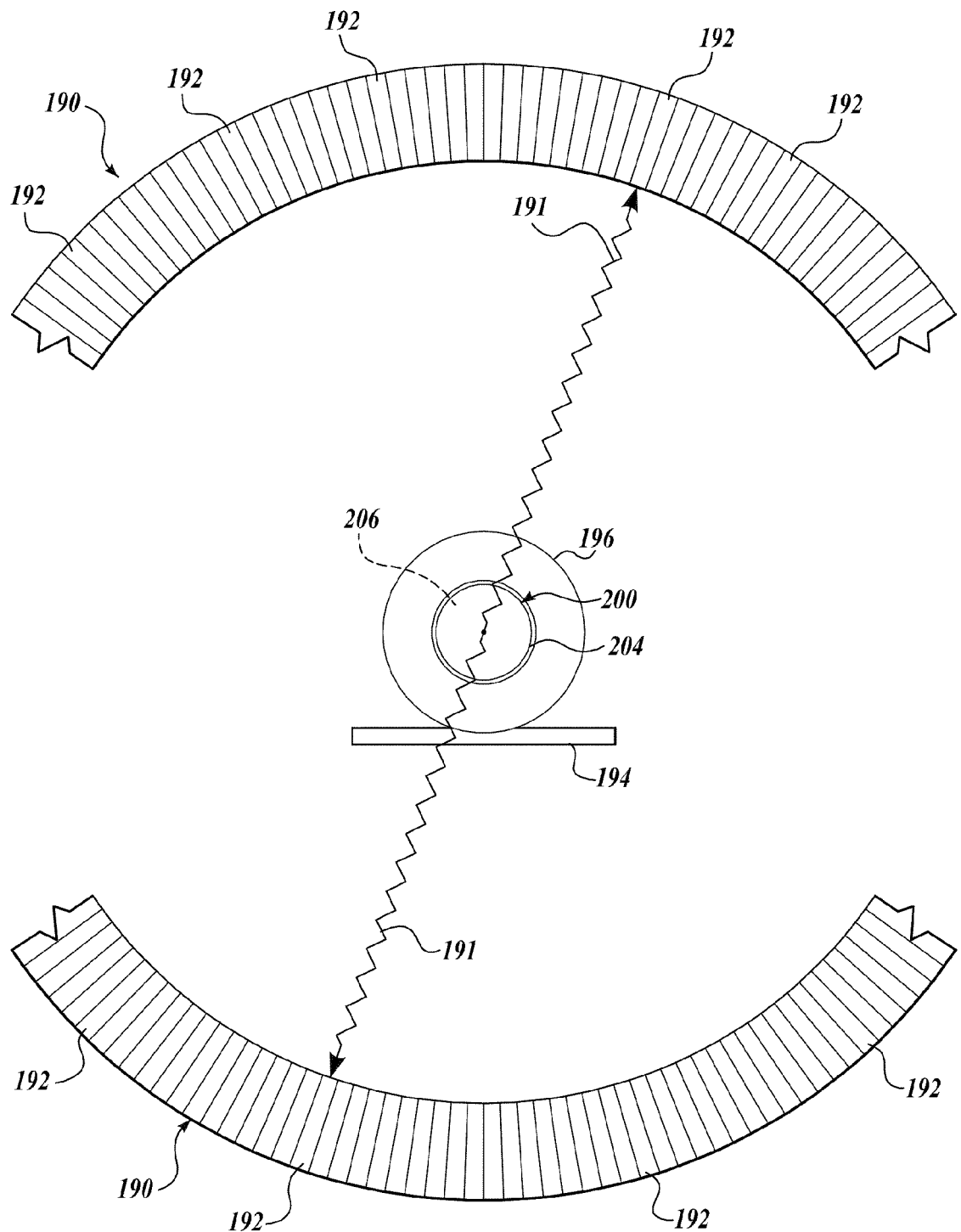
FIG. 5 shows a schematic view of a positron emission tomography scanner with a PET source standard in accordance with the present invention disposed in a phantom placed within the imaging region of the scanner.

FIG. 5 illustrates schematically a PET scanner having oppositely disposed ring segments 190, each segment including an array of detector elements 192. PET detectors are well-known in the art, and the specifics of the PET detectors are not relevant to the present invention. Therefore the detector elements 192 will not be described in detail here. The detection technique relies on the coincident detection of the pair of photons 191 to identify valid signals. A representative coincident pair is illustrated in FIG. 5. In general, photons that are not considered coincident unless they are detected within a few nanoseconds of each other.

When a coincident pair of photons 191 are detected by detector elements 192 within the detector element's field of view, a straight line through the locations in the detectors where the photons 191 are detected is called the line of response ("LOR"). The corresponding positron emission that generated the photons 191 is presumed to lie along the LOR. The PET scanner uses the pair detection events and the LORs to map the location and density of tracer isotope within the body. The resulting map shows where the tracer isotope has become concentrated, identifying regions of metabolic activity in the body.

Typically, the resulting images show the relative concentration of the radioisotope in the scanned tissue, which provides important medical information about the patient, and may be sufficient to qualitatively identify regions of interest in a particular patient, at a particular time. However, it is currently difficult or impossible to determine the absolute amount of radioisotope that has been concentrated at particular regions and tissues. It would be beneficial to be able to quantitatively characterize the amount of radionuclide that has been concentrated in particular tissues, e.g., to quantify the metabolic activity in the tissue. For example, when comparing different PET images taken at different times to determine the efficacy of a particular coarse of treatment, it would be helpful to be able to quantitatively compare the amount of radionuclide concentrated in the tissue of interest. As another example, in studies involving multiple subjects, perhaps located at different institutions, it would be helpful to be able to quantify the concentration of radionuclide between various PET images.

FIG. 5 also shows a container or phantom 196 located on a table or support platform 194 within the scanner's region of interest. PET phantoms 196 are well-known in the art. An exemplary suitable phantom is the ACR Phantom available from Data Spectrum Corporation of Hillsborough, N.C. A PET calibration source 200 in accordance with the present invention is disposed within the phantom 196. The PET calibration source 200 includes a container 204 containing a precisely measured quantity of a radionuclide dispersed within a matrix material 206 (radionuclide/matrix). In a current embodiment the radionuclide is Ge-68. As used herein, Ge-68 is used conventionally to include germanium-68 with gallium-68. The container 204 is mounted on a plate 202 (FIG. 6) that is sized to fit within the phantom 196, thereby fixing the position of the container 204 within the phantom 196. Optionally, the phantom 196 may be water-filled, and may include a background level of radioactive material (e.g., fluorine-18) in the water to simulate the normal imaging environment.

Figure 6:
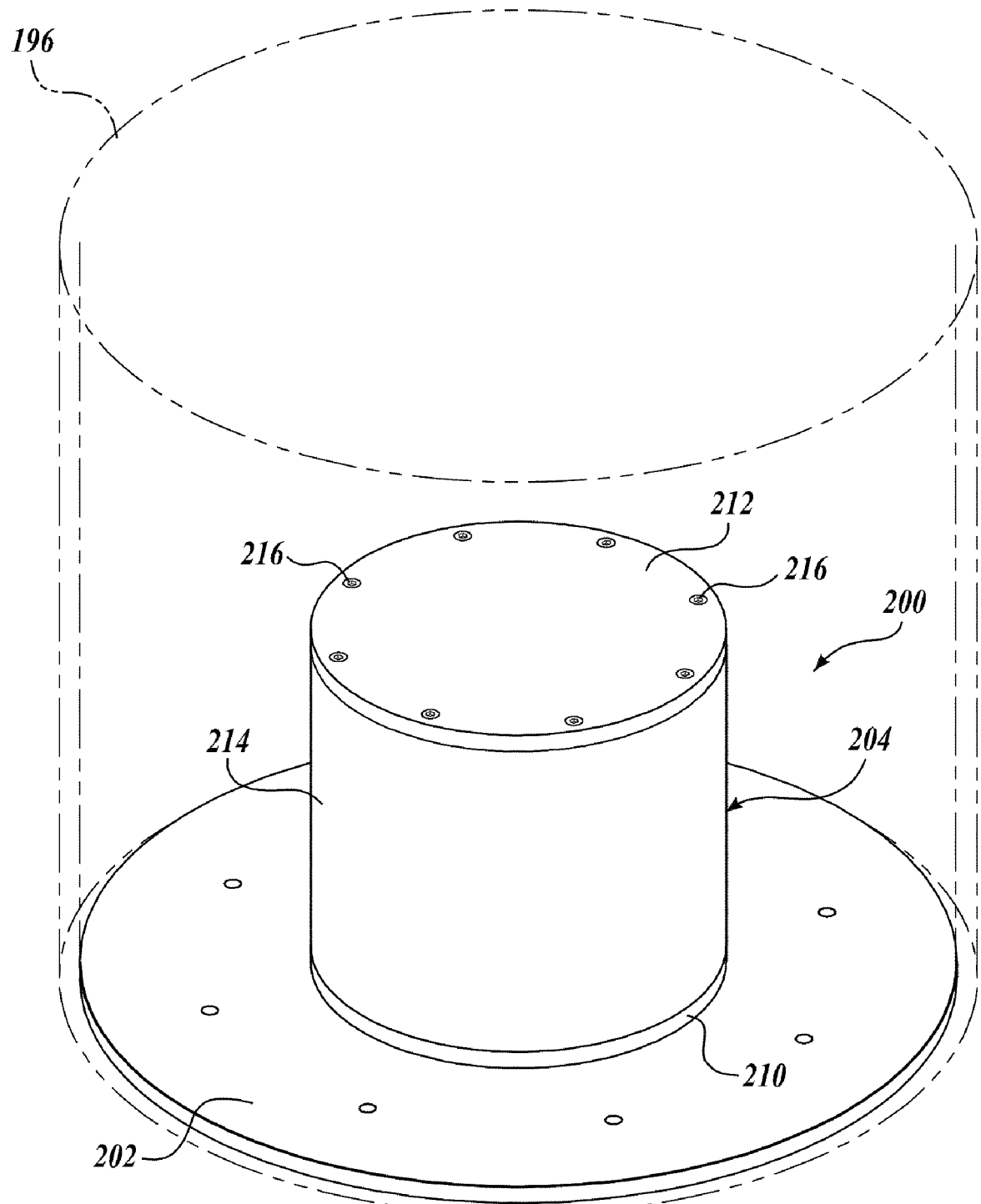
FIG. 6 shows a view of the PET source standard shown in FIG. 5 attached to a support plate and ready for placement in a phantom.

FIG. 6 shows a perspective view of the PET calibration source 200 with the phantom 196 indicated in dashed line. In the current embodiment, the container 204 includes a cylindrical tubular outer wall 214, a top wall 212 attached with attachment members 216 to close the top of the outer wall 214, and a bottom wall 210 attached to close the bottom of the outer wall 214. The container is fixed to the plate 202, for example with attachment members (not shown). The container 204 may be formed from any suitable material. In a current embodiment the outer wall 214, top wall 212, bottom wall 210 and plate 202 are formed from a high density polyethylene (HDPE) or the equivalent.

Figure 7:
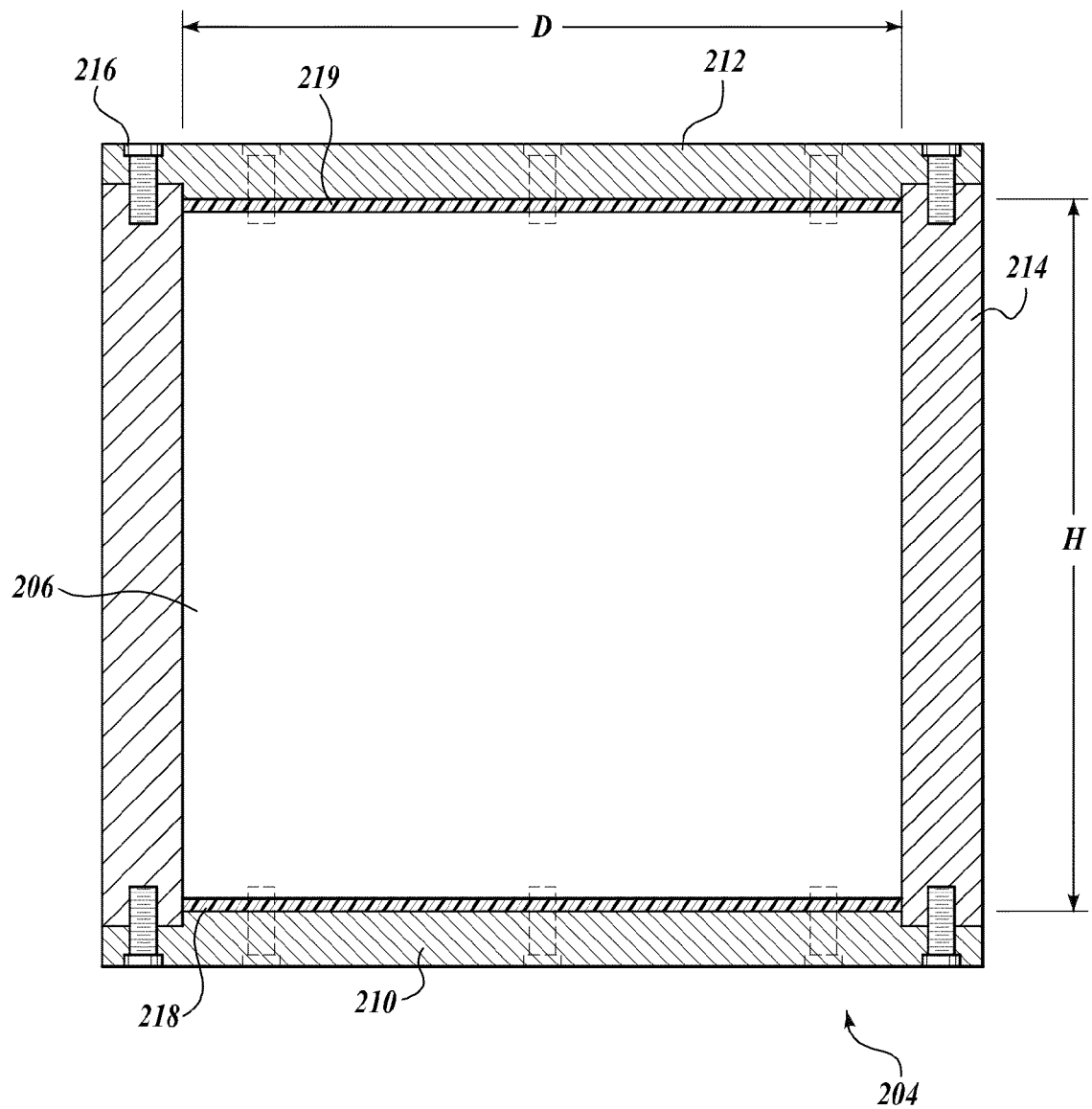
FIG. 7 shows a cross sectional side view of the PET source standard shown in FIG. 5.

A cross-sectional side view of the container 204, including the radionuclide/matrix 206 is shown in FIG. 7. In this embodiment a bottom seal layers 218 formed as a thin layer of epoxy, and a similar top seal layer 219, are provided over and below the radionuclide/matrix 206, to ensure that the radionuclide/matrix 206 is securely sealed within the container 204.

Referring again to FIG. 5, the PET calibration source 200, is placed in a water-filled phantom 196, and positioned within the PET scanner. The scanner is then operated, preferable according to a standard patient protocol.

The partial volume effect is a known effect that can bias the measured intensity in PET scanners, e.g., near the edges of scanned objects. The partial volume effect primarily results from: 1) Image blurring introduced by the finite spatial resolution of the imaging system; and 2) Image sampling error caused by voxel averaging of detected intensity, sometimes referred to as the sampling effect.

For example, a typical PET scanner the partial volume effect may significantly bias the measured intensity for detected regions that are within about 2 cm of the edge of a source. For PET scanner calibration it is desirable that the PET calibration source 200 be large enough to select an interior region of interest that is disposed far enough away from the edges of the radionuclide/matrix 206 to avoid the partial volume effect. Therefore, for purposes of calibrating the intensity of the PET scanner measurements with the known radioactivity of the radionuclide/matrix 206 mixture, it is desirable that the volume of the radionuclide/matrix 206 be large enough to provide an interior region of interest that is disposed far enough away from the edges of the radionuclide/matrix 206 edges to avoid or mitigate the partial volume effect.

In an exemplary embodiment, for a PET scanner having a spatial resolution of about 2 cm, the PET calibration source 200 is large enough to provide a region of interest that is more than two centimeters from any edge. In the current embodiment of the PET calibration source aliquot 200 the cylindrical volume enclosed by the container 204, e.g., approximately the volume of the radionuclide/matrix 206, has a diameter D of 6 cm, and a height H of 6 cm. When the PET calibration source 200 is placed in the phantom 196 and scanned, the measured intensity of a core region approximately 2 cm in diameter and 2 cm high can be used to correlate the measured intensity with the known radioactivity of the radionuclide/matrix 206. It will be appreciated, however, that the particular size of the radionuclide/matrix 206 may be different, depending on the imaging capabilities of a particular PET scanner.

A method and system for absolute calibration of a PET system will now be described. In the present method a calibrator aliquot, for example the calibrator source standard 10 shown in FIG. 1 or the equivalent, and a PET calibration source 200 are obtained, wherein the radionuclide/matrix 22 in the calibrator source aliquot 10 and the radionuclide/matrix 206 in the PET calibration source 200 are both taken from the same batch or reservoir of well-mixed radionuclide/matrix material such that the radionuclide/matrix 22 and the radionuclide/matrix 206 are known to be identical in radioactivity density. Preferably the radionuclide/matrix material in the aliquots 10 and 200 comprise a uniform solid matrix containing Ge-68/Ga-68 that is cross-calibrated to one or more positron-emitting radionuclides, for example fluorine-18 (F-18), nitrogen-13 (N-13), carbon-11 (C-11), and/or oxygen-15 (O-15).

In an alternative embodiment, the calibrator source aliquot 10 and the radionuclide/matrix 206 in the PET calibration source 200 are both taken from separate reservoirs of well-mixed radionuclide/matrix material wherein the radionuclide/matrix 22 and the radionuclide/matrix 206 are carefully cross-calibrated to each other, such that the radioactivity density of the radionuclide/matrix 206 can be determined to a desired accuracy from the measured radioactivity density of the radionuclide/matrix 22. For example, PET calibration source radionuclide/matrix 206 may be formed with half the radioactivity density of the calibrator source radionuclide/matrix 22. In this alternate embodiment the useful lifetime of the system may be increased, albeit with an corresponding increase in overall uncertainty. In the subsequent discussion, it is assumed that the two radionuclide/matrix sources 22 and 206 are taken from a single reservoir. It will be obvious to persons of skill in the art how the method may be modified to use the alternate embodiment.

In an exemplary procedure, the dose calibrator 36 (FIG. 2) ion chamber setting is adjusted for correct Ge-68 measurement using a Ge-68 dose calibrator source standard, as discussed above, wherein the dose calibrator source standard is directly traceable to NIST. In this exemplary procedure the dose calibrator source standard used to calibrate the calibrator 36 is similar to, but separate from, the dose calibrator aliquot 10 used for the PET calibration procedure. The dose calibrator aliquot 10 is then placed on the ion chamber syringe scoop 46, and positioned for measurement in the dose calibrator 36 ion chamber 54. A reading is taken of the radioactivity measured in the calibrator source aliquot 10. The PET calibration source 200, which is mounted inside the water-filled phantom 196 is placed in the PET scanner and scanned, using a standard patient protocol. The images obtained from the scan are reconstructed and a measurement of the radioactivity concentration in a center portion of the radionuclide/matrix 206 is recorded based on the intensity of the image. The center portion may comprise a centered cylinder about 2 cm high and having a diameter of about 2 cm. The radioactivity concentration in the center portion of the radionuclide/matrix 206 is then correlated directly to the reading taken from the dose calibrator 36 for the calibrator aliquot 10, since the radioactivity concentration of the dose calibrator aliquot 10 is identical to the radioactivity concentration of the PET calibrator source aliquot 200.

Figure 8:
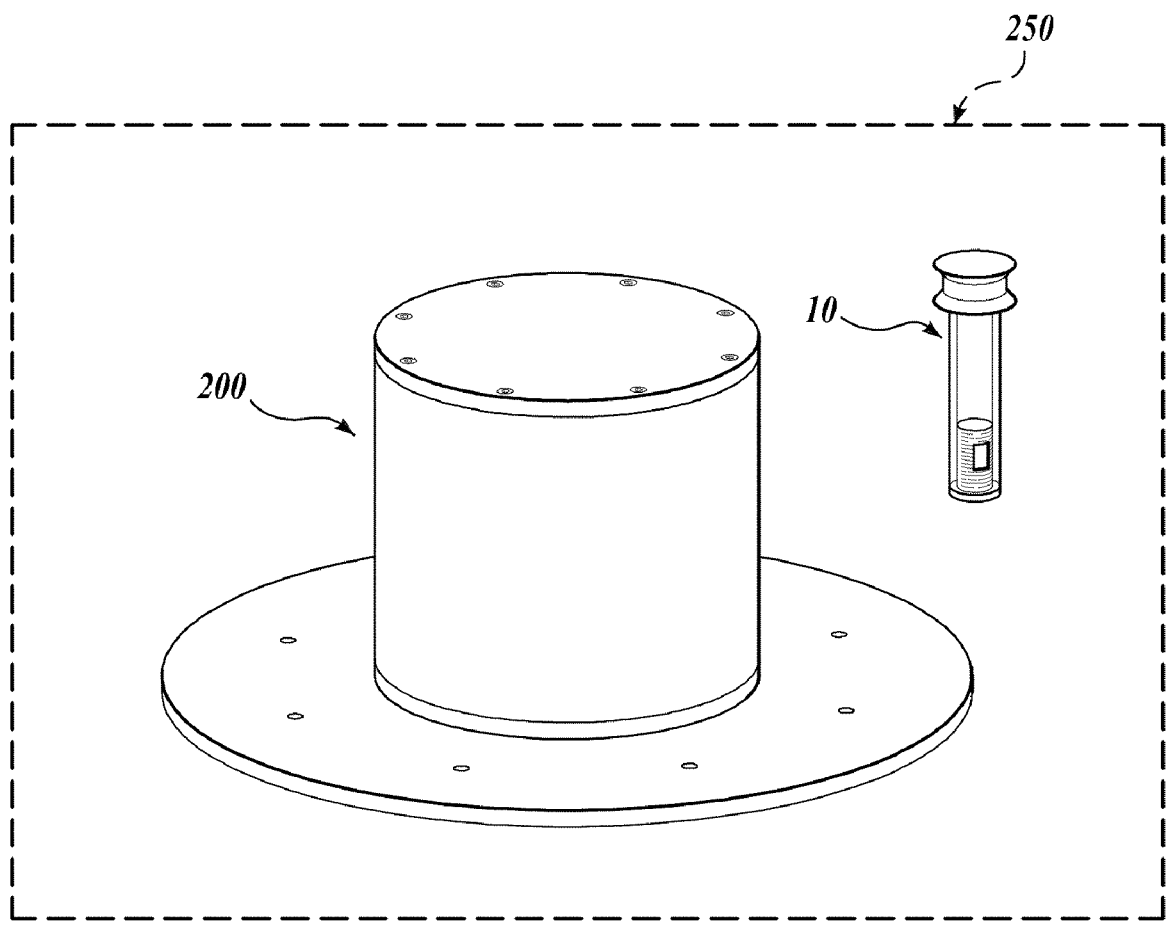
FIG. 8 shows a PET system calibration kit in accordance with the present invention.

As illustrated in FIG. 8, it is contemplated that the calibrator source aliquot 10 and the PET calibration source 200, both containing the radionuclide/matrix 206 obtained from a the same batch of mixed radionuclide/matrix material, may be packaged together as a kit 250. The kit 250 would be provided in a package to a PET scanner operator, with suitable markings (not shown) to ensure the aliquot 10 and source 200 are identifiable as being obtained from the same source. An operator would typically have a suitable dose calibrator 36, and could therefore use the kit 250 to calibrate the PET scanner.

Although the currently preferred system and kit use the same reservoir source for the radionuclide/matrix for the calibrator aliquot 10 and the PET calibration source 200, it is contemplated by the present invention that alternatively two separate radionuclide/matrix reservoirs may be used, wherein the radionuclide/matrix reservoirs are cross-calibrated such that the radioactivity in the PET calibration source 200 can be inferred from measurements taken of the calibrator aliquot 10.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for calibrating a positron emission tomography scanner comprising the steps:
   a) obtaining a calibrator source aliquot and a PET calibration source wherein the calibrator source aliquot and the PET calibration source each contain a radionuclide dispersed within a matrix obtained from a single reservoir of the radionuclide dispersed within the matrix material;
   b) placing the calibrator source aliquot in a dose calibrator;
   c) measuring the radioactivity density in the calibrator source aliquot with the dose calibrator;
   d) placing the PET calibration source in a phantom;
   e) scanning the PET calibration source in a PET scanner;
   f) correlating a measured intensity obtained from the step of scanning the PET calibration source with the measured radioactivity density in the calibrator source aliquot; and
   g) using this comparison to calibrate the PET scanner.

2. The method of claim 1, further comprising the step of first calibrating the dose calibrator with a dose calibrator source standard that is directly traceable to a standard from the National Institute of Standards and Technology.

3. The method of claim 1, wherein the matrix comprises an epoxy.

4. The method of claim 1, wherein the radionuclide comprises germanium 68.

5. The method of claim 1, wherein the radioactivity of the radionuclide dispersed within the matrix material is cross calibrated to at least one of fluorine-18, nitrogen-13, carbon-11 and oxygen-15.

6. The method of claim 1, wherein the PET calibration source comprises a cylinder of the radionuclide dispersed within the matrix material having a diameter of about 6 cm.

7. The method of claim 6, wherein the cylinder of radionuclide dispersed within the matrix material is about 6 cm long.

8. The method of claim 7, wherein the PET calibration source further comprises a cylindrical container enclosing the cylinder of radionuclide dispersed within the matrix material, the cylindrical container formed from a high density polyethylene.

9. A system for calibrating a PET scanner comprising a calibrator source aliquot sized and configured to be received in a dose calibrator, the calibrator source aliquot containing a first solid quantity of a radionuclide dispersed within a matrix material, and a PET calibration source sized and configured to be received in a PET scanner, the PET calibration source containing a second solid quantity of the radionuclide dispersed in the matrix material, wherein the first and second solid quantities are obtained from a single batch of the radionuclide dispersed in the matrix material, such that the first and second solid quantities have identical radioactivity densities.

10. The system of claim 9, wherein the second solid quantity of the radionuclide dispersed in the matrix material comprises a cylinder that is approximately 6 cm in diameter.

11. The system of claim 9, wherein the matrix material comprises an epoxy.

12. The system of claim 9, wherein the radionuclide comprises germanium 68.

13. The system of claim 9, wherein the radioactivity of the second solid quantity of the radionuclide dispersed in the matrix material is cross calibrated to at least one of fluorine-18, nitrogen-13, carbon-11 and oxygen-15.

14. The system of claim 9, wherein the second solid quantity of the radionuclide dispersed in a matrix material is disposed in a cylindrical container formed from high density polyethylene.

15. The system of claim 14, wherein the container is attached to a circular plate sized to fit within a phantom.

16. A kit for calibrating a positron emission tomography scanner comprising:
   a dose calibrator source aliquot comprising a container filled with a first quantity of a radionuclide dispersed in a matrix material; and
   a PET calibration source aliquot comprising a container filled with a second quantity of the radionuclide dispersed in the matrix material;
   wherein the first quantity and the second quantity of the radionuclide dispersed in the matrix material are taken from a single reservoir of the radionuclide dispersed in the matrix material.

17. The kit for calibrating a positron emission tomography scanner of claim 16, wherein the radionuclide dispersed in the matrix material comprising a uniform solid matrix containing Ge-68/Ga-68 that is cross calibrated to at least one of F-18, N-13, C-11 and O-15.

18. A system for calibrating a PET scanner comprising a calibrator source aliquot sized and configured to be received in a dose calibrator, the calibrator source aliquot containing a first solid quantity of a first radionuclide dispersed within a first matrix material, and a PET calibration source sized and configured to be received in a PET scanner, the PET calibration source containing a second solid quantity of a second radionuclide dispersed in a second matrix material, wherein the first solid quantity is calibrated to the second solid quantity such that the radioactivity density of the second solid quantity can be determined from a measurement of the radioactivity density of the first solid quantity.

19. The system of claim 18, wherein the first and second radionuclides are germanium 68.

20. The system of claim 18, wherein the matrix material comprises an epoxy.

21. The system of claim 18, wherein the radioactivity of the second solid quantity of the radionuclide dispersed in the matrix material is cross calibrated to at least one of fluorine-18, nitrogen-13, carbon-11 and oxygen-15.

* * * * *